(12) United States Patent
Staric et al.

(10) Patent No.: US 10,357,431 B2
(45) Date of Patent: Jul. 23, 2019

(54) PROCESS FOR THE PREPARATION OF A PHARMACEUTICAL COMPOSITION COMPRISING A LOW SOLUBLE PHARMACEUTICALLY ACTIVE INGREDIENT

(75) Inventors: Rok Staric, Ljubljana (SI); Simon Skubin, Ljubljana (SI); Miha Homar, Ljubljana (SI); Bostjan Markun, Ljubljana (SI); Sandra Berglez, Ljubljana (SI); Petra Kralj, Ljubljana (SI); Marija Boskovic, Ljubljana (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 712 days.

(21) Appl. No.: 13/996,330

(22) PCT Filed: Dec. 21, 2011

(86) PCT No.: PCT/EP2011/073569
§ 371 (c)(1),
(2), (4) Date: Aug. 28, 2013

(87) PCT Pub. No.: WO2012/085071
PCT Pub. Date: Jun. 28, 2012

(65) Prior Publication Data
US 2013/0338131 A1    Dec. 19, 2013

(30) Foreign Application Priority Data
Dec. 22, 2010   (EP) .................................... 10015940

(51) Int. Cl.
| A61K 31/397 | (2006.01) |
|---|---|
| A61J 3/00 | (2006.01) |
| A61K 9/20 | (2006.01) |
| A61K 31/192 | (2006.01) |
| A61K 31/216 | (2006.01) |
| A61K 31/366 | (2006.01) |
| A61K 31/40 | (2006.01) |
| A61K 31/4184 | (2006.01) |
| A61K 31/436 | (2006.01) |
| A61K 31/635 | (2006.01) |

(52) U.S. Cl.
CPC ............... *A61J 3/00* (2013.01); *A61K 9/2018* (2013.01); *A61K 9/2054* (2013.01); *A61K 9/2095* (2013.01); *A61K 31/192* (2013.01); *A61K 31/216* (2013.01); *A61K 31/366* (2013.01); *A61K 31/397* (2013.01); *A61K 31/40* (2013.01); *A61K 31/4184* (2013.01); *A61K 31/436* (2013.01); *A61K 31/635* (2013.01)

(58) Field of Classification Search
CPC .................................................... A61K 31/397
See application file for complete search history.

(56) References Cited

U.S. PATENT DOCUMENTS

| 4,540,602 | A | 9/1985 | Motoyama |
|---|---|---|---|
| 2004/0087640 | A1 | 5/2004 | Ferro |
| 2004/0126423 | A1 | 7/2004 | Moore et al. |
| 2007/0027218 | A1* | 2/2007 | Jain et al. ..................... 514/724 |
| 2007/0275052 | A1 | 11/2007 | Mahajan et al. |
| 2008/0279928 | A1 | 11/2008 | Moschwitzer |
| 2010/0234342 | A1* | 9/2010 | Cifter ................... A61K 9/2018 |
| | | | 514/210.02 |

FOREIGN PATENT DOCUMENTS

| EP | 2 016 938 A1 | 1/2009 |
|---|---|---|
| EP | 2016938 A1 * | 1/2009 |
| EP | 2 095 816 A1 | 9/2009 |
| EP | 2 216 016 A1 | 8/2010 |
| WO | WO 95/31974 A1 | 11/1995 |
| WO | WO 2006/060698 A1 | 6/2006 |
| WO | WO 2007/003365 A1 | 1/2007 |
| WO | WO 2008/101723 A2 | 8/2008 |
| WO | WO 2008101723 A2 * | 8/2008 |
| WO | WO 2009074286 A2 * | 6/2009 |
| WO | WO-2009074286 A2 * | 6/2009 ........... A61K 9/2018 |

OTHER PUBLICATIONS

IUPAC Gold Book. "Suspension." © Nov. 11, 2007. Available from: < http://web.archive.org/web/20071111193548/http://goldbook.iupac.org/S06198.html >.*
ChemSpider. "Ezetimibe," © 2014. Available from: < http://www.chemspider.com/Chemical-Structure.132493.html >.*
Dictionary.com. "Lactose." © 2002. Available from: < http://dictionary.reference.com/browse/lactose >.*
Drugs.com/ "Hypromellose." (c) 2000. Available from: < http://www.drugs.com/inactive/hypromellose-369.html >.*
PubChem. "Ezetimibe." (c) 2018. Accessed Jun. 21, 2018. Available from: < https://pubchem.ncbi.nim.nih.gov/compound/Ezetimibe >. (Year: 2018).*
International Search Report & Written Opinion issued in PCT/EP2011/073569, dated Mar. 27, 2012, 12 pages.

* cited by examiner

*Primary Examiner* — Andrew D Kosar
*Assistant Examiner* — John S Kenyon
(74) *Attorney, Agent, or Firm* — Arent Fox LLP

(57) ABSTRACT

A pharmaceutical composition having a pharmaceutically active ingredient (API) that is poorly soluble in water, the pharmaceutical composition obtained by a process, which generates a dosage form containing the pharmaceutical composition. Use of the generated dosage form for the treatment of hypercholesterolemia.

16 Claims, 1 Drawing Sheet

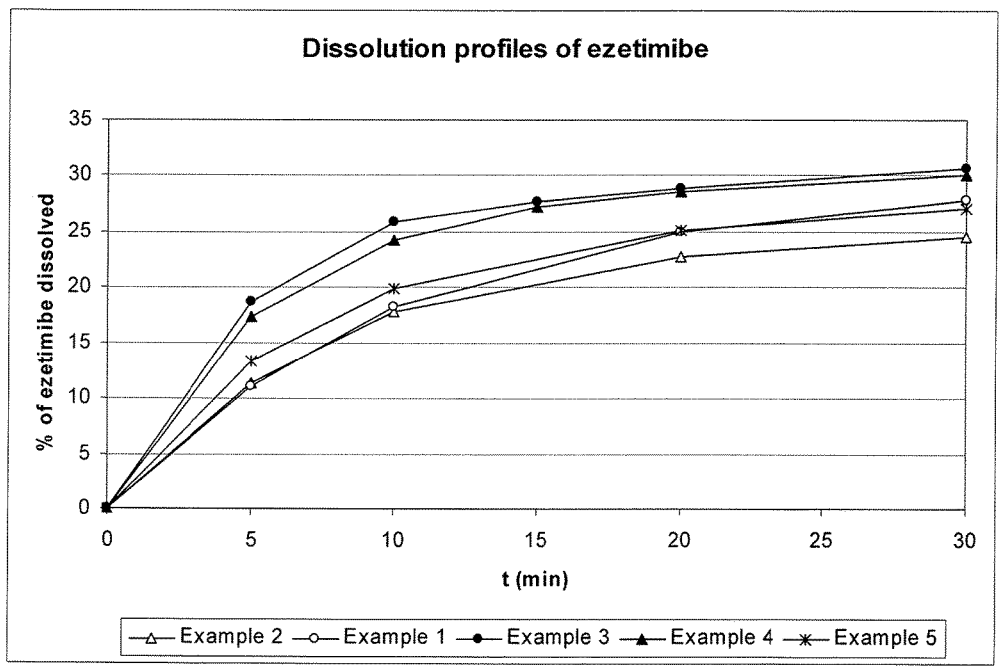

PROCESS FOR THE PREPARATION OF A PHARMACEUTICAL COMPOSITION COMPRISING A LOW SOLUBLE PHARMACEUTICALLY ACTIVE INGREDIENT

CROSS-REFERENCE TO RELATED APPLICATION

This application is a National Stage entry of International Application No. PCT/EP2011/073569, filed Dec. 21, 2011, which claims priority to European Application No. 10015940.9, filed Dec. 22, 2010, the entire specifications, claims and drawings of which are incorporated herewith by reference.

FIELD OF THE INVENTION

The present invention belongs to the field of pharmaceutical industry and relates to a process for preparing a pharmaceutical composition comprising a pharmaceutically active ingredient (API) that is poorly soluble in water, a pharmaceutical composition obtained according to said process, to a dosage forms comprising said pharmaceutical composition and to the use of said dosage forms for the treatment of hypercholesterolemia.

DESCRIPTION OF THE BACKGROUND ART

Pharmaceutically active ingredients (API) that are poorly soluble constitute a problem for many reasons, e.g. due to the slow dissolution profile of said API, when incorporated. For instance, when a pharmaceutical composition comprising an API being poorly soluble in water is taken orally, the drug must dissolve in aqueous gastrointestinal fluids, such as in patients' stomach or intestine, before it can exert a therapeutic effect. An API being "poorly soluble in water" is generally considered to be an API which has a solubility of less than or equal to 0.1 mg/ml in water as defined in the US or European Pharmacopoeia. A recurring problem with pharmaceutical compositions comprising poorly water soluble drugs is that the rate of dissolution of the drug limits its biological availability. Reduction of particle size (e.g. by micronization) is one of the most common methods used to increase the dissolution profiles of poorly soluble active ingredients.

In order to demonstrate such problems of representative critical situations and attempts to deal with such situations represented by the use of ezetimibe as an exemplified API being poorly soluble API in water, reference can for example be made to the following documents.

US 2007/0275052 discloses pharmaceutical compositions containing micronized particles of ezetimibe, and a process for preparing said pharmaceutical compositions. In this process, ezetimibe is blended with further ingredients, and the resulting blend was granulated with a binding solution to get granules. The granules were dried and finally compressed into tablets.

By further exemplified reference to another representative situation, EP 2 216 016 describes the dry preparation of a mixture containing the pharmaceutically active ingredient (API) ezetimibe, by sieving and mixing ezetimibe with hydrophilic excipients, by avoiding the use of water and organic solvents.

As a further exemplified reference, US 2004/0126423 A1 discloses a composition comprising a cholesterol absorption inhibitor and a HMG-CoA reductase inhibitor, one or more anti-oxidants, microcrystalline cellulose, hydroxypropyl methylcellulose (HPMC), magnesium stearate and lactose.

Another illustrative reference, WO 2007/003365, discloses pharmaceutical compositions, inter alia comprising ezetimibe as API. In preparing said compositions, it is described that the API is mixed with one or more controlled release agents and granulated by adding solvent in a shear mixer or by fluidized bed granulator. The resulting granulate is then dried and sized.

Still further illustrative WO 2008/101723 shows a pharmaceutical composition comprising ezetimibe and at least one hydrophilic polymer, wherein said ingredients are dissolved in organic solvent, followed by drying or and an optional step of further milling, sieving and filling into capsules or compressing into tablets, or wherein the solution is dispersed onto a suitable carrier.

However, despite the above described methods and preparations of formulations containing a poorly soluble API, there is a need for an improved process for the preparation of a pharmaceutical composition or dosage form, respectively, containing an API being poorly soluble in water, and for an improved pharmaceutical composition or dosage form, respectively, containing said API.

SUMMARY OF THE INVENTION

The present invention provides the following aspects, subject-matters and preferred embodiments, which respectively taken alone or in combination, further contribute to solving the object of the present invention:

(1) A process for preparing a pharmaceutical composition comprising particles of a pharmaceutically active ingredient (API), wherein the solubility of said API is less or equal to 0.1 mg/ml in water, or even less or equal to 0.01 mg/ml in water, the process comprising the steps of:
a) providing a suspension comprising API particles and one or more excipients,
b) subjecting the suspension provided by step a) to a high energy input treatment, so that essentially no agglomerates are present in the suspension,
c) further processing the suspension by high shear granulation, fluid bed granulation, spray drying or lyophilisation.

(2) The process according to item (1), wherein the high energy input treatment is selected from rotor-stator mixing, ultrasound treatment, ball milling, and high energy mixing. Furthermore, high pressure homogenizer such as EmulsiFlex C3 at 300-1500 bar can be used.

(3) The process according to item (1) or (2), wherein after step (c) a further step (d) of formulating the pharmaceutical composition into a dosage form is carried out.

(4) Process according to any of the preceding items, wherein the particle size distribution d(0.5) of the API particles, preferably of the primary particles of the API, that is present after step (b) and prior to step (c), after step (c) and prior to step (d), and/or after step (d), corresponds essentially to or is smaller than the primary particle size distribution d(0.5) of the API that is used for providing the suspension of step (a).

In other words, the particle size distribution d(0.5) is assessed after step (b) and prior to step (c), after step (c) and prior to step (d), and/or after step (d), and compared with the primary particle size distribution d(0.5) of the API that is used for providing the suspension of step (a). According to the invention, the d(0.5) particle size distribution does not essentially increase during steps (a), (b), (c), and/or (d). Preferably, the particle size distribution thus does not essentially increase during all steps (a)-(d).

(5) Process according to any of the preceding claims, wherein the primary particle size distribution d(0.5) of the API that is used for providing the suspension of step (a) is less than about 5 μm, preferably equal to or less than about 4 μm, and more preferably equal to or less than about 3 μm.

(6) Process according to any of the preceding items, wherein during step (b) optionally the primary particle size is reduced.

(7) The process according to any of the preceding items, wherein the API is selected from the group of poorly soluble APIs consisting of ketoprofen, sirolimus, celecoxib, candesartan, atorvastatin, simvastatin, ezetimibe, fenofibrate, and the like, preferably the API is ezetimibe, optionally ezetimibe is combined with simvastatin. Optionally, the aforementioned API may be combined with any other API independent of the other API's solubility in water.

(8) Process according to any of the preceding items, wherein the suspension of step a) comprises excipients selected from the group consisting of hydrophilic excipients and polymers, preferably the polymers are cellulose derivatives.

(9) Process according to the preceding item, wherein the hydrophilic excipient is selected from the group consisting of polyethylene glycols, poloxamers, polyols, inorganic salts (e.g. sodium chloride and the like), polysaccharides, saccharides or mixtures thereof (e.g. StarLac® or IsoMalt®), lactose, spray dried lactose and starch, preferably the hydrophilic excipient is selected from the group consisting of lactose, spray dried lactose and starch, more preferably the hydrophilic excipient is lactose, and
wherein the polymer is selected from the group consisting of polyvinyl alcohol, polyvinylpyrrolidone, gelatin or cellulose derivative such as methylcellulose, ethylcellulose, hydroxypropylmethylcellulose, carboxymethyl cellulose and hydroxypropylcellulose, preferably the cellulose derivative is hydroxypropylmethylcellulose. Preferably, the hydrophilic excipient is hypromellose and/or lactose.

(10) Process according to any of the preceding items, wherein the suspension of step (a) only contains, as excipients, the excipients lactose and hydroxypropylmethylcellulose.

(11) Process according to any of the preceding items, wherein step (a) comprises the step of:
a1) providing a solution containing one or more excipients as defined in any of items (8) to (10),
a2) suspending the API as defined in item (7) in the solution of step a1),
a3) homogenizing the resulting suspension.

(12) Process according to item (11), wherein the homogenizing is carried out by applying propeller mixing, rapid mixer granulation or high shear granulation.

(13) Process according to any of the preceding items, wherein in step (c) the suspension resulting from step (b) is spray dried by spraying the suspension onto a carrier, thereby obtaining the pharmaceutical composition, preferably the suspension is sprayed onto the carrier in a fluidized bed process.

With regard to this item (13), in order to analyze whether the pharmaceutical preparation has been prepared by spraying the suspension onto a carrier, or whether a high shear granulation, fluid bed granulation or lyophilisation has been carried out in step (c), various suitable methods that are known to a person skilled in the art can be applied, such as SEM (scanning electron microscope) imaging or Raman spectroscopy. Raman spectroscopy for instance offers the possibility to visually locate different components being present, e.g. the carrier and the API. If the API is present on the carrier evenly distributed, it can be concluded that the suspension comprising the API has been sprayed onto the carrier.

(14) Process according to item (13), wherein the suitable carrier is selected from the group consisting of lactose, such as lactose monohydrate and anhydrous lactose; starch and starch derivatives; mannitol; xylitol; sorbitol; cellulose such as microcrystalline cellulose and powdered cellulose; magnesium stearate; silica colloidal anhydrous; croscarmellose sodium; and mixtures thereof; preferably, the suitable carrier is selected from microcrystalline cellulose, croscarmellose sodium, lactose and/or their mixtures.

(15) Process according to any of the previous items wherein, in addition to the API that is present in the suspension of step (a), a further API is used.

(16) Process according to any of the preceding items, wherein the further API is used during any of steps (a) to (d), preferably after step (a), and more preferably after step (b).

(17) Process according to any of the preceding items, wherein during step (a), preferably during steps (a) and (b), only one API, preferably ezetimibe, is used.

(18) Process according to any of items (15) to (17), wherein the further API is selected from the group of poorly soluble compounds consisting of ketoprofen, sirolimus, celecoxib, candesartan, atorvastatin, simvastatin, and the like, preferably the further API is simvastatin.

(19) Process according to any of the previous items, wherein during any of steps (a) to (d), preferably after step (a), more preferably after step (b), at least one further excipient is added.

(20) Process according to item (19), wherein the at least one further excipient is selected from the group consisting of diluents, binding agents, fillers, disintegrants, lubricants, sweeteners, glidants, flavourings and colouring agents.

(21) Process according to item (20), wherein the fillers are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous or spray dried lactose, calcium, such as calcium hydrogen phosphate, sorbitol, and xylitol, particularly preferred, the fillers are selected from the group consisting of pregelatinized starch, microcrystalline cellulose, silicified microcrystalline cellulose, lactose monohydrate, and spray dried lactose;
the disintegrants are selected from the group consisting of carmellose calcium, carboxymethylstarch sodium, croscarmellose sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrants are selected from the group consisting of sodium starch glycolate, croscarmellose sodium salt, and croscarmellose sodium;
the lubricants are selected from the group consisting of stearic acid, talc, sodium stearyl fumarate and magnesium stearate, particularly preferred, the lubricant is magnesium stearate;
the binding agents are selected from the group consisting of polyvinyl pyrrolidone (Povidone), copolymers of vinylpyrrolidone with other vinyl derivatives (Copovidone), hydroxypropyl methylcellulose, methylcellulose, hydroxypropylcellulose, powdered acacia, gelatin, guar gum, carbomer, such as carbopol, polymethacrylates and starch, particularly preferred, the binding agents are selected from the group consisting of hydroxypropyl methylcellulose, hydroxypropylcellulose and copovidone;
the diluents are selected from carbohydrates such as monosaccharides like glucose, oligosaccharides like sucrose, anhydrous lactose and lactose monohydrate, and sugar alcohols like sorbitol, mannitol, erythritol, and xylitol, particularly preferred the diluent is sorbitol;
the glidants are selected from the group consisting of colloidal silica, hydrophobic colloidal silica and magnesium trisilicate, such as talcum, particularly preferred the glidants are selected from the group consisting of colloidal silica and hydrophobic colloidal silica; and/or the sweeteners are selected from the group consisting of aspartame, saccharin sodium, dipotassium glycyrrhizinate, aspartame, stevia, thaumatin, and the like.

(22) Process according to any of items (3) to (21), wherein the dosage form is in solid form, including tablets, capsules (soft or hard capsules), caplets, lozenges, and sachets, preferably the dosage form is a tablet.

(23) Process according to item (22), wherein the dosage form, preferably the tablet, comprises a coating.

The coating may comprise components that are conventionally used for coating dosage purposes; preferably, said components are selected from the group consisting of polymers including cellulose derivatives (e.g. hypromellose), povidone, polyvinyl alcohol, polyethylene glycol and insoluble compounds including titanium dioxide, pigments, lakes and talc. Preferably, the coating comprises hypromellose, polyethylene glycol, talc and suitable pigments.

(24) A pharmaceutical composition obtained by a process according to any of the preceding items.

As disclosed herein, such a pharmaceutical composition contains essentially no agglomerates. This is due to the application of steps (b) and (c) when preparing such a pharmaceutical composition, i.e. the subjection of a suspension provided by step (a) to a high energy input treatment (step b) and by further processing the suspension by high shear granulation, fluid bed granulation, spray drying or lyophilization (step c). As disclosed elsewhere herein, further processing the suspension by spraying the suspension onto a carrier in step (c) is preferred. Whether the pharmaceutical composition has been prepared by spraying the suspension onto a carrier or whether the pharmaceutical composition has been prepared by applying a high shear granulation, fluid bed granulation or lyophilization, can be determined as described above (item (13)).

With regard to the term "essentially no agglomerates", reference is made to the description below. In order to determine whether essentially no agglomerates are present in the pharmaceutical composition, reference is made to the description below ((A), (B) and (C)). Therein, optical methods are described that allow for assessing the size of individual particles, such as SEM, or Raman spectroscopy. Alternatively, or in addition to the methods described in (A), (B) and (C), dissolution tests may be carried out (see description below) in order to assess the extent of agglomeration in a pharmaceutical composition or final dosage form, respectively.

(25) A pharmaceutical composition comprising particles of a pharmaceutically active ingredient (API), wherein the solubility of said API in water is less or equal to 0.1 mg/ml as defined in the US or European Pharmacopoeia, and wherein essentially no agglomerates of primary API particles are present in said composition.

Regarding the definition of "essentially no agglomerates" of primary API particles are present in said composition, reference is made to the description provided herein.

(26) The pharmaceutical composition according to item (25), wherein the particle size distribution d(0.5) of the API is less than 5 µm, preferably equal to or less than 4 µm, and more preferably equal to or less than 3 µm.

(27) The pharmaceutical composition according to item (25) or (26), wherein the API is selected from the group consisting of poorly soluble APIs consisting of ketoprofen, sirolimus, celecoxib, candesartan, atorvastatin, simvastatin, ezetimibe, fenofibrate, and the like, preferably the API is ezetimibe.

(28) A dosage form, comprising the pharmaceutical composition according to any of the preceding items.

(29) Use of the dosage form of item (28) for the treatment of hypercholesterolemia, wherein the API is ezetimibe, optionally combined with simvastatin.

DETAILED DESCRIPTION OF THE INVENTION

The present invention is now described in more detail by preferred embodiments and examples, which are however presented for illustrative purpose only and shall not be understood as limiting the scope of the present invention in any way.

It was surprisingly found that the inventive process, comprising the steps of subjecting a suspension comprising an API that is poorly soluble in water and further comprising one or more excipients, to a high energy input treatment, more specifically applying high energy input capable of deagglomeration, preferably to high energy mixing or ultrasound treatment, and further processing the suspension by high shear granulation, fluid bed granulation, spray drying or lyophilization, can provide improved pharmaceutical compositions or dosage forms, wherein the improvement is for example indicated by an improved dissolution profile. Moreover, the inventive process represents an improved process, for example in terms of processability.

One of the most common methods used to increase the dissolution profile of poorly soluble APIs is the reduction of particle size of said API. Therefore, in order to provide pharmaceutical compositions or dosage forms exhibiting satisfying and sufficient dissolution profiles, and, therefore, acceptable therapeutic effects, it is common practice to reduce the size of the API particles until a particle size is reached of which it is assumed that it exhibits a satisfying dissolution profile. Such a reduction of particle sizes of API can for instance be achieved by micronization, such as milling or grinding. However, micronized drug powders are very cohesive, due to the micronization processes causing significant dislocation of crystal structure on the particle surface. Such micronized or size-reduced particles tend to (re-) agglomerate during processing, thereby forming so-called "secondary particles", i.e. agglomerates, which in turn leads to even poorer dissolution performance. Such agglomerates, each agglomerate being a secondary particle, consist essentially of a plurality of so-called "primary particles". Furthermore, with even more decreasing particle size, the attraction forces between the (primary) particles that finally form agglomerates increase more and more and, as a consequence, it is more and more difficult to break down the formed agglomerates to initial particle size, that is the size of the particles prior to their agglomeration (i.e. the size of the primary particles). Surprisingly and distinct from conventional methods, the process according to the present invention allows obtaining improved dissolution performance of poorly soluble API while starting the process with appropriate primary particle sizes thereof, even if the initial particle size of the primary API particle that is used may be very small, for example being smaller than a critical particle size where agglomeration is generated, such as e.g. having a d(0.5) of less than 10 µm, or less than 5 µm, or even smaller d(0.5) levels. The primary particles, with which the process according to the present invention is started, can be present in an agglomerated or deagglomerated state. In typical cases the primary particles may be present in an agglomerated state, i.e. a priori forming agglomerates or so-called secondary particles. It is assumed that by applying the process according to the present invention, essentially all of the agglomerated particles (i.e. secondary particles) are deagglomerated under appropriate conditions and then further processed in a particular manner to maintain the essentially or completely deagglomerated state, thereby resulting in an enhanced pharmaceutical composition, that e.g. exhibits an enhanced dissolution profile and, therefore, exhibits an enhanced bioavailability.

A further advantage of the process according to the present invention is that it allows the use of wet granulation. Wet granulation may be a preferred method in pharmaceutical industry, as it provides for better prospects in terms of ease of processing, especially with respect to the required flow and cohesive properties. Further, wet granulation prevents the segregation of the ingredients. However, just wet granulation in general has a relatively high tendency to convert primary particles into larger, physically strong agglomerates (secondary particles). This tendency is further exaggerated by a decreasing particle size, thereby e.g. leading to (even more) unsatisfying dissolution rates. However, despite applying wet granulation techniques as a preferred embodiment, using the method according to claim 1 surprisingly provides for enhanced pharmaceutical compositions e.g. exhibiting satisfying enhanced dissolution profiles of the API.

According to the present invention, the term "high energy input treatment" denotes a method where high energy, preferably high mechanical energy, is applied to the suspension comprising the API. The high energy input treatment within the meaning of the present invention is effective to, or capable of, deagglomerating particle agglomerates. Preferably the high energy input treatment is selected from ball milling, ultrasound treatment, rotor-stator mixing, and high energy mixing. Desirably the conditions of the treatment are set to enable deagglomeration. According to the present invention, the use of a high energy input treatment results in essentially no agglomerates being present in the suspension after said treatment.

For carrying out the high energy input treatment, for instance a ball mill can be used. Such a ball mill is e.g. the Fryma Koruma ball mill, being equipped with a ball size of 0.4-2 mm, and applying a rotor speed of 5-15 m/s and a pump speed of 20-100 rpm. For ultrasound treatment, a conventional ultrasound bath or flow through ultra sound device can be used. Rotor-stator treatment can e.g. be carried out by using an Ultraturrax at a rotation speed of 5000-15000 rpm. Furthermore, high pressure homogenizer such as EmulsiFlex C3 at 300-1500 bar can be used.

The use of a high shear granulation, rapid mixer granulation, propeller mixing or the like treatment, which is incapable of deagglomerating essentially all agglomerates being present in the suspension provided by step (a), does not represent a high energy input treatment, however may be used in addition, when applied preferably prior to, the high energy input treatment in order to enhance homogenization of the suspension of particles or in order to dissolve polymers, if desired.

Unexpectedly, the method according to claim 1, i.e. the provision of a suspension comprising poorly soluble API and one or more excipients, and subjecting said suspension to a high energy input treatment, followed by further processing said suspension as indicated herein provides for enhanced pharmaceutical compositions and dosage forms, respectively, e.g. exhibiting satisfying, enhanced dissolution profiles of the API.

The API used according to the present invention is poorly soluble in water. The term "poorly soluble in water", which may even be denoted as "practically insoluble in water", defines that the solubility of the API is less or equal to 0.1 mg/ml in water, or even less or equal to 0.01 mg/ml in water, or even less or equal to 0.001 mg/ml in water. Whether an API is "practically insoluble" in a solvent such as water can e.g. be determined according to the U.S. Pharmacopeia (U.S.P.) XXI (page 1441). Therein, an API is defined as being "practically insoluble" if one part of solute requires more than 10,000 parts of solvent to dissolve it or its solubility is less than 0.1 mg/ml of solvent. Additionally, or alternatively, the API whose solubility has to be determined is mixed for 24 h in water or alternatively in buffer at 37° C., followed by measuring the amount of dissolved API. The amount of dissolved API can for instance be measured by applying HPLC (high pressure liquid chromatography).

Provided that this solubility criterion is met, the API can be selected from the group consisting of proteins, peptides, nucleotides, anti-obesity drugs, nutraceuticals, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, antiretroviral drugs from the protease inhibitor class, immunosuppressants, antithyroid agents, antiviral agents, anxiolytics, sedatives, astringents, beta-adrenoreceptor blocking agents, blood products and substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, non-steroidal anti-inflammatory drugs (NSAIDs), parasympathomimetics, parathyroid calcitonin and bisphosphonates, prostaglandins, radio-pharmaceuticals, sex hormones, anti-allergic agents, stimulants and anorectics, sympathomimetics, thyroid agents, vasodilators, xanthines, tadalafil, fenofibrate, cholecalciferol (vitamin D), simvastatin, ezetimibe, ketoprofen, celecoxib, candesartan, atorvastatin, sirolimus, NSAIDs such as naproxen and ibuprofen, megestrol acetate, ritonavir (HIV protease inhibitor), or cyclosporine.

Preferably, the API within the meaning of the present invention is selected from the group consisting of tadalafil, fenofibrate, cholecalciferol (vitamin D), simvastatin, ezetimibe, ketoprofen, celecoxib, candesartan, atorvastatin, sirolimus, NSAIDs such as naproxen and ibuprofen, megestrol acetate, ritonavir (HIV protease inhibitor), or cyclosporine; or any API mixture thereof. More preferably, the API is selected from the group consisting of fenofibrate, cholecalciferol (vitamin D), simvastatin, ezetimibe, ketoprofen, celecoxib, candesartan, atorvastatin, and sirolimus. Even more preferred, the API is selected from the group consisting of ezetimibe and simvastatin, respectively alone or in combination, and even more preferably the used API is ezetimibe.

Ezetimibe is a white crystalline powder and is indicated mainly for primary hypercholesterolemia (administered alone or in combination with e.g. an HMG-CoA reductase inhibitor), homozygous familial hypercholesterolemia (administered with the APIs atorvastatin or simvastatin) and homozygous sitosterolemia. Hypercholesterolemia has been implicated in atherosclerosis, heart attack, and stroke and is one of several conditions that may lead to coronary artery disease, which is the leading cause of death in the United States, accounting for approximately 600,000 deaths per year. The risk group includes the overweight, smokers, those with a poor diet (e.g. one rich in saturated fats), those who take inadequate exercise and suffering from stress. For such risk individuals, as well as those tested and found to have unduly high plasma cholesterol levels, a variety of treatments have been proposed, e.g. changes in diet and habits, increased exercise, etc. However, such treatments are not always easy to enforce and there exist a need for improved medicinal treatments which are effective at reducing plasma cholesterol levels. In above mentioned cases, ezetimibe can be prescribed, since it is indicated mainly for primary hypercholesterolemia (administered alone or in combination with an HMG-CoA reductase inhibitor), homozygous familial hypercholesterolemia (administered with atorvastatin or simvastatin) and homozygous sitosterolemia.

Ezetimibe is reported to be freely to very soluble in ethanol, methanol, and acetone, however particularly poorly soluble in water. Because of the suitability of ezetimibe to be used for the treatment of a broad spectrum of common disease states, there is in particular a need for this API to exhibit enhanced dissolution profiles when administered to a subject in need thereof, e.g. when taken orally. The process according to the present invention is particularly useful for providing a pharmaceutical composition exhibiting an improved dissolution profile of ezetimibe. As the advantage of the present invention can be applied to other APIs being poorly soluble in water, the present invention is however not limited to ezetimibe or ezetimibe/further API combinations.

In a further embodiment according to the present invention, it is also possible to use a combination of two or more APIs, in particular it is possible to combine the practically insoluble APIs according to the invention with one or more other APIs, which can have any solubility, including being very soluble in water. Whether an API is "very soluble" in a solvent such as water can e.g. be determined according to the U.S. Pharmacopoeia. Therein, an API is defined as being "very soluble" if one part of solute requires less than 1 part of solvent to dissolve it, or if its solubility is more or equal to 1000 mg/ml in water.

APIs having various solubilities in water and suitable as a further API can for instance be selected from the group consisting of abacavir, acamprosate, acebrophylline, aceclofenac, acemetacin, acenocoumarol, acetylcysteine, acetyl-L-carnitine, acetylsalicylic acid, aciclovir, acitazanolast, acitretin, adapalene, adefovir dipivoxil, ademetionine, agomelatine, albendazole, alclometasone, alendronic acid, alfacalcidol, alfuzosin, alibendol, aliskiren, allopurinol, almotriptan, alosetron, alprazolam, alprostadil, alteplase, alvimopan, ambrisentan, ambroxol, amifampridine, amifostine, amikacin, amiodarone, amisulpride, amitriptyline, amlodipine, amorolfine, amoxicillin, amphotericin B, ampicillin, anastrozole, anecortave, anidulafungin, aniracetam, antofloxacin, aprepitant, aprotinin, arbidol, arformoterol, argatroban, aripiprazole, armodafinil, artemether, artesunate, ascorbic acid, asenapin, atazanavir, atenolol, atomoxetine, atorvastatin, atosiban, atovaquone, azacitidine, azapentacene, azasetron, azathioprine, azelastine, azelnidipine, azithromycin, azlocillin, aztreonam, bacitracin, baclofen, balsalazide, barnidipine, basiliximab, batroxobin, bazedoxifen, beclomethasone, benazepril, bendroflumethiazide, benidipine, benzydamine, bepridil, beraprost, besifloxacin, betamethasone, betaxolol, bevacizumab, bexarotene, bezafibrate, biapenem, bicalutamide, bifonazole, bimatoprost, bisoprolol, bivalirudin, blonanserin, bortezomib, bosentan, brimonidine, brinzolamide, brivudine, bromazepam, bromfenac, bromhexine, bromocriptine, bromopride, brotizolam, budesonide, buflomedil, buprenorphine, bupropion, buproprion, buserelin, buspirone, busulfan, butamirate, butoconazole, cabergoline, calcipotriol, calcitriol, calcium dobesilate, calcium levofolinate, camostat, candesartan cilexetil, capecitabine, captopril, carbamazepine, carbimazole, carbocisteine, carbomer, carboplatin, carperitide, carvedilol, caspofungin, cefaclor, cefadroxil, cefalexin, cefalotin, cefathiamidine, cefazedone, cefazolin, cefcapene pivoxil, cefdinir, cefditoren pivoxil, cefepime, cefetamet pivoxil, cefixime, cefmenoxime, cefminox, cefotaxime, cefotiam, cefovecin, cefpiramide, cefpodoxime proxetil, cefprozil, ceftazidime, ceftezole, ceftizoxime, ceftobiprol medocaril, ceftriaxone, cefuroxime, cefuroxime axetil, celecoxib, celiprolol, cetirizine, cetuximab, cevimeline, chlorhexidine, chloropyramine, chlorphenamine, chlortalidone, chlorzoxazone, ciclesonide, ciclopirox, ciclosporin, cilazapril, cilnidipine, cilostazol, cimetidine, cinacalcet, cinepazet, ciprofloxacin, cisatracurium besylate, cisplatin, citalopram, citicoline, clarithromycin, clevidipine, clevudine, clindamycin, clobenzorex, clobetasol, clobutinol, clodronic acid, clofarabin, clomipramine, clonazepam, clonidine, cloperastine, clopidogrel, clotrimazol, cloxazolam, clozapine, cobamamide, codeine, colistin, conivaptan, corticotropin, cromoglicic acid, cyclobenzaprine, cyproterone, cytarabine, dabigatran, danaparoid, dantrolene, dapoxetin, daptomycin, darifenacin, darunavir, dasatinib, decitabin, deferasirox, deferiprone, degarelix, desflurane, desloratadine, desmopressin, desogestrel, desoximetasone, desvenlafaxine, dexamethasone, dexibuprofen, dexlansopril, dexmedetomidine, dexmethylphenidate, dexpanthenol, dexrazoxane, diacerein, diatrizoic acid, diazepam, diclofenac, didanosine, dienogest, diflunisal, digoxin, diltiazem, dimemorfan, dimenhydrinate, dimethicone, dinoprostone, diphenhydramine, dipyridamole, docetaxel, dolasetron, domperidone, donepezil, doripenem, dornase alfa, dorzolamide, doxazosin, doxercalciferol, doxofylline, doxorubicin, doxycycline, doxylamine, dronabinol, dronedarone, dropropizine, drotaverine, duloxetine, dutasteride, ebastine, eberconazole, ecallantide, econazole, edaravone, efalizumab, efavirenz, eflornithine, eicosapentaenoic acid, elcatonin, eletriptan, eltrombopag, emtricitabine, enalapril, enfuvirtide, entacapone, entecavir, epairestat, eperisone, ephedrine, epinastine, epinephrine, epirubicin, eplerenone, eprosartan, eptifibatide, erdosteine, erlosamide, erlotinib, ertapenem, erythromycin, escitalopram, eslicarbazepine, esomeprazole, estradiol, eszopiclone, etamsylate, etifoxine, etimicin, etizolam, etodolac, etofenamate, etonogestrel, etoposide, etoricoxib, etravidine, everolimus, exemestane, exenatide, ezetimibe, famciclovir, famotidine, febuxostat, felbinac, felodipine, fenofibrate, fenspiride, fentanyl, fenticonazole, fesoterodine, fexofenadine, finasteride, flecainide, flomoxef, flucloxacillin, fluconazole, fludarabine, fluindione, flunisolide, fluocinonide, fluorometholone, fluorouracil, fluoxetine, flupirtine, flurbiprofen, fluticason furoate, fluticasone, fluvastatin, fluvoxamine, follitropin beta, fondaparinux, formoterol, fosamprenavir, fosaprepitant, foscarnet sodium, fosfluconazole, fosfomycin, fosinopril, fosphenytoin, fospropofol, frovatriptan, fudosteine, fulvestrant, furosemide, fusidic acid, gabapentin, gaenoxacin, galantamine, ganirelix, gatifloxacin, gefitinib, gemcitabine, gemfibrozil, gemifloxacin, gentamicin, glibenclamide, gliclazide, glimepiride, glipizide, gliquidone, glycopyrronium hydroxide, goserelin, granisetron, grepafloxacin, guaifenesin, haloperidol, helicidine, hydralazine, hydrochlorothiazide, hydrocortisone, hydromorphone, hydroxocobalamin, hydroxychloroquine, hydroxyzine, ibandronic acid, ibuprofen, icatibant, iloperidon, imatinib, imidafenacin, imidapril, imiquimod, indacaterol, indapamide, indometacin, ipratropium bromide, irbesartan, irinotecan, isoconazole, isoniazid, isosorbide dinitrate, isothipendyl, isotretinoin, isradipine, itraconazole, ivabradine, ivermectin, ixabepilon, kanamycin, ketanserin, ketoconazole, ketoprofen, ketorolac, ketotifen, lacidipine, lactulose, lamivudine, lamotrigine, lanoconazole, lanreotide, lansoprazole, lanthanum carbonate, lapatinib, lasofoxifen, latanoprost, leflunomide, lenalidomide, lentinan, lercanidipine, letrozole, leuprorelin, levetiracetam, levobupivacaine, levocabastine, levocarnitine, levocetirizine, levodropropizine, levofloxacin, levomethadone, levonorgestrel, levosalbutamol, levosimendan, levosulpiride, levothyroxine sodium, lidocaine, limaprost, linezolid, liraglutide, lisdexamfetamine, lisinopril, lofepramine, loperamide, loratadine, lorazepam, lormetazepam, losartan, loteprednol, lovastatin, loxoprofen, lubiprostone, luliconazole, lymecycline, malathion, manidipine, maraviroc, maxacalcitol, mebeverine, mecasermin, meclofenoxate, mecobalamin, medroxyprogesterone, mefenamic acid, megestrol, meloxicam, melphalan, mequitazine, meropenem, mesalazine, metamizole sodium, metaxalone, metformin, methadone, methisopril, methocarbamol, methotrexate, methylnaltrexone, methylphenidate, methylprednisolone, metoclopramide, metopimazine, metoprolol, metronidazole, mexidol, micafungin, miconazole, midazolam, mifepristone, mildronate, milnacipran, minocycline, minodronate, minoxidil, miriplatin, mirtazapine, mitiglinide, mitotane, modafinil, molsidomine, mometasone, montelukast, morniflumate, morphine, mosapride, moxifloxacin, moxonidine, mozavaptane, mupirocin, mycophenolate mofetil, nabilone, nabumetone, nadifloxacin, nafamostat, nafcillin, naftifine, naftopidil, nalfurafine, naphazoline, naproxen, naratriptan, natamycin, nateglinide, nedaplatin, nefopam, nelarabine, nelfinavir, nepafenac, nesiritide, nevirapine, nicardipine, nicergoline, nicorandil, nifedipine, nilotinib, nimesulide, nimodipine, nisoldipine, nitrofural, nitrofurantoin, nitroxoline, nizatidine, norepinephrine, norethisterone, norfloxacin, noscapine, nystatin, ofloxacin, olanzapine, olmesartan medoxomil, olopatadine, omalizumab, omeprazole, ondansetron, opipramol, orlistat, ornidazole, oseltamivir, otilonium, oxaliplatin, oxaprozin, oxcarbazepine, oxiconazole, oxiracetam, oxybutynin, oxycodone, oxymetazoline, oxytetracycline, ozagrel, paclitaxel, paliperidone, palivizumab, palonosetron, pamidronic acid, pantoprazole, paracetamol, paricalcitol, paroxetine, pazopanib, pazufloxacin, pemetrexed, pemirolast, pentobarbital, pentostatin, pentoxifylline, peramivir, pergolide, perindopril, perospirone, phendimetrazine, phenylbutyrate, phenylephrine, phenytoin, pholcodine, pidotimod, pilsicainide, pimecrolimus, pinaverium bromide, pioglitazone, piperacillin, piracetam, pirfenidone, piroxicam, pitavastatin, pivmecillinam, plerixafor, posaconazole, pralatrexate, pramipexole, pramlintide, pranlukast, prasugrel, pravastatin, prednisolone, prednisone, pregabalin, primidone, pristinamycin, procarbazine, progesterone, promazine, promestriene, promethazine, propafenone, propiverine, propofol, propranolol, prucalopride, prulifloxacin, quetiapine, quinapril, rabeprazole, racecadotril, raloxifene, raltegravir, ramatroban, ramelteon, ramipril, ranibizumab, ranitidine, ranolazine, rebamipide, regadenoson, remifentanil, repaglinide, revaprazan, ribavirin, rifampicin, rifamycin, rifaximin, riluzole, risedronate, risperidone, ritonavir, rituximab, rivaroxaban, rivastigmin, rizatriptan, rocuronium bromide, romidepsin, romiplostim, ropinirole, ropivacaine, rosiglitazone, rosuvastatin, rotigotine, roxithromycin, rufinamide, rupatadine, salbutamol, salcatonin, salmeterol, saquinavir, sargramostim, sarpogrelate, saxagliptin, scopolamine, secnidazole, selegiline, sertaconazole, sertindole, sertraline, sevoflurane, sibutramine, sildenafil, silodosin, simvastatin, sincalide, sirolimus, sitafloxacin, sitagliptin, sitaxentan, sivelestat, solifenacin, somatropin, sorafenib, sotalol, spiramycin, spironolactone, stavudine, stiripentol, sulbactam, sulfacetamide, sulfasalazine, sulodexide, sulpiride, sultamicillin, sumatriptan, sunitinib, suplatast tosilate, tacrolimus, tadalafil, tafluprost, talniflumate, taltirelin, tamibarotene, tamoxifen, tamsulosin, tapentadol, tazarotene, tebipenem, teceleukin, tedisamil, tegafur, tegaserod, teicoplanin, telavancin, telbivudin, telithromycin, telmisartan, temazepam, temozolomide, temsirolimus, tenofovir disoproxil, tenoxicam, teprenone, terazosin, terbinafine, terbutaline, teriparatide, terlipressin, testosterone, tetrabenazine, tetracosactide, thalidomide, theophylline, tiagabine, tianeptine, tibolone, ticlopidine, tigecycline, timolol, tiotropium bromide, tipepidine, tipranavir, tiropramide, tizanidine, tobramycin, tolperisone, tolterodine, tolvaptan, topiramate, topotecan, torasemide, trabestedine, tramadol, tramazoline, trandolapril, tranexamic acid, tranilast, travoprost, trazodone, tretinoin, triamcinolone acetonide, triazolam, tribenoside, trimebutine, trimetazidine, trimethoprim, triptorelin, trospium hydroxide, troxerutin, tulobuterol, ubenimex, udenafil, ulprisnil, urapidil, ursodeoxycholic acid, valaciclovir, valganciclovir, valproate semisodium, valproic acid, valsartan, vancomycin, vardenafil, varenicline, venlafaxine, verapamil, verteporfin, vildagliptin, vinflunine, vinorelbine, vinpocetine, voriconazole, warfarin, xylometazoline, zaleplon, ziconotide, zileuton, ziprasidone, zofenopril, zoledronic acid, zolmitriptan, zolpidem, zonisamide, zopiclone, zotarolimus.

Accordingly, in addition to the (first) API that is present in the suspension of step (a), a further (second) API may be present. The further (second) API may be added to the pharmaceutical composition at any stage of the process, i.e. during any of steps (a) to (d). In one embodiment of the invention, the further API(s) is/are added to the suspension during step (a) or step (b). In another embodiment, the further API(s) is/are sprayed onto a carrier in a separate process by using one or more further suspension(s)/solution(s) comprising the further API(s). It is also possible to add the further API(s) in dry form to the dried pharmaceutical composition obtained in step (c) or (d).

Preferably, the further (second) API(s) is/are added after step (a), and more preferably after step (b). The further API that is added to the pharmaceutical composition can be selected from the group consisting of API that are practically insoluble in water as defined above, or from the group consisting of API that are soluble in water as defined above. The further API that can be added preferably is different from the API that is present in the suspension of step (a). In a preferred embodiment, the further API is selected from the group consisting of API that are practically insoluble in water, as described elsewhere herein. Preferably, the further API is simvastatin.

In one embodiment of the process according to the present invention, during step (a), preferably during steps (a) and (b), only one API is present in the suspension. Preferably, this API is selected from the group consisting of API that are practically insoluble in water as discussed above.

In a further preferred embodiment according to the present invention, the APIs being present in the pharmaceutical composition or dosage form, respectively, are ezetimibe and simvastatin.

In a particularly exemplified embodiment according to the present invention, the particle size distribution d(0.5) that is present after step (b) and prior to step (c), after step (c) and prior to step (d), and/or after step (d), corresponds essentially to or is smaller than the primary particle size distribution d(0.5) of the API that is used for providing the suspension of step (a). This (further) contributes to a further improved pharmaceutical composition or dosage form, respectively, as e.g. the dissolution profile and controllability are further enhanced. In general, the particle size distribution of a powder, or granular material, or particles e.g. dispersed in fluid, is a list of values or a mathematical function that defines the relative amounts of particles present, sorted according to size. The nomenclature describing the particle size distribution is herein referred to as "d(0.5)". For example, a d(0.5) of 5 µm means that 50% (by volume) of the particles have a size less than or equal to 5 µm, as tested by any conventional method such as laser diffraction method (e.g. laser diffraction Malvern). When measuring the particle size distribution by laser diffraction Malvern, an appropriate amount of sample (usually a few drops of suspension) is put into a gently mixing chamber filled with water. From this chamber, the sample continuously flows through a measuring chamber and the particle size distribution is determined by laser diffraction. Within the meaning of the present invention, the term "particle size distribution d(0.5) corresponds essentially to or is smaller than" denotes that (i) the particle size distribution d(0.5) of the primary particles when measured after deagglomeration, i.e. after the high energy input treatment has been applied to the suspension containing the API particles, essentially corresponds to the particle size distribution d(0.5) of the primary particles that were used for providing the suspension of step (a); or (ii), alternatively, it denotes that the particle size distribution d(0.5) when measured after deagglomeration is smaller than the particle size distribution d(0.5) of the primary particles that were used for providing the suspension of step (a).

As to alternative (i), the term "particle size distribution d(0.5) corresponds essentially to" more specifically denotes that the particle size distribution d(0.5) of the primary particles when measured after deagglomeration corresponds to at least 70%, or at least 75%, preferably at least 80%, more preferably at least 85%, even more preferably at least 90%, and most preferably at least 95% or at least 97% of the particle size distribution d(0.5) of the primary particles that were used for providing the suspension of step a).

The particle size distribution d(0.5) of the primary API particles can be assessed and compared at the following time points:

A) Particle size distribution d(0.5) of the primary particles used for preparing the suspension of step a) (first measurement) compared with the particle size distribution d(0.5) of the primary particles after the deagglomeration step, i.e. after step (b), however prior to step c) (second measurement);

B) Particle size distribution d(0.5) of the primary particles used for preparing the suspension of step (a) (first measurement) compared with the particle size distribution d(0.5) of the primary particles after the deagglomeration step and after step (c), however prior to step (d) (second measurement);

C) Particle size distribution d(0.5) of the primary particles used for preparing the suspension of step (a) (first measurement) compared with the particle size distribution d(0.5) of the primary particles being present in the final dosage form (second measurement).

The particle size distribution d(0.5) of the primary API particles used for providing the suspension of step (a) in (A), (B) and (C) can be assessed by any method that is known to a person skilled in the art, such as by using laser diffraction method (e.g. Malvern Mastersizer, see above). As described elsewhere herein, said primary API particles may be present deagglomerated, however said particles may also be present in an agglomerated state. In the latter case, it is also possible to determine the particle size distribution d(0.5) by laser diffraction. If appropriate, it is preferred that the method for carrying out the first measurement corresponds to the method used for carrying out the second measurement.

In case (A), the particle size distribution d(0.5) of the primary particles after the deagglomeration step, i.e. after step (b), however prior to step (c), can be measured by any suitable method that is known to a person skilled in the art, e.g. by laser diffraction, by photoanalysis, or by optical (counting) methods such as microscopic analysis or automated analysis of electron micrographs. When applying such an optical method, e.g. a suspension image can be recorded and the particle size distribution (such as d(0.5)) can be determined by means of a particle recognition software. An optical method comprises the steps of sample preparation (which usually is applying the suspension to be analyzed on a suitable surface, e.g. glass for optical and carbon tape for electron micrographs), imaging (or observing) the sample, manually or automatically assessing the size of individual particles, and statistical analysis of the data.

In case B), the particle size distribution d(0.5) of the primary particles after the deagglomeration step and after step (c), however prior to step (d), can be measured by any suitable method that is known to a person skilled in the art, e.g. by the methods as described for (A) and for (C).

In case (C), the particle size distribution d(0.5) of the primary particles being present in the final dosage form can be measured by any suitable method that is known to a person skilled in the art, e.g. by the methods as described above for (A) and (B). A preferred method is analyzing the final dosage form microscopically, e.g. by using an SEM (scanning electron microscope). For this purpose, the final dosage form, e.g. the tablet, is divided into small pieces that can be analyzed by SEM. By using a suitable magnification, the size of a representative number of API particles can be determined and conclusions can be drawn as to the particle size distribution d(0.5) of the API particles that are present in the final dosage form.

When assessing microscopically the particle size distribution, e.g. a recorded image (more preferably disintegrated tablet suspension is recorded under visual microscope) is processed with particle recognition software in order to obtain a particle size distribution estimation. Alternatively, Raman microscopy can be used, a picture is taken and the API particle size is measured. The protocol is similar to the protocol used when applying an SEM.

The method according to the present invention is particularly useful for processing API particles having a particle size distribution d(0.5) that is relatively small, e.g. a particle size distribution d(0.5) where agglomeration is generated (critical particle size/particle size distribution). The critical particle size/particle size distribution for a selected API is known to a person skilled in the art. Further, said size/size distribution can be determined by any suitable method that is known to a person skilled in the art, such as by using SEM or laser diffraction. Usually SEM or more preferably disintegrated tablet suspension is recorded under a visual microscope and is processed with particle recognition software to obtain an estimation of particle size distribution. On SEM pictures, eventually occurring agglomerates are also visible. When using laser diffraction, a suspension of the API is transferred to the dispersing chamber containing water. The sample is gently stirred and pumped through the apparatus, and the particle size is measured in the laser diffraction apparatus. Further, ultrasound is applied on the sample and the particle size is measured again. The first measurement corresponds to the agglomerate size, the second one to the primary particle size. If there is no difference, no agglomeration is present. The method might have to be optimized for individual samples (e.g. with regard to circulation time, ultrasound strength and duration, and the like) to obtain accurate results.

Preferably, the particle size distribution d(0.5) of the API that is used for providing the suspension of step (a) is less than 5 µm, preferably equal to or less than 4 µm, and more preferably equal to or less than 3 µm. In addition, the particle size distribution d(0.5) of the API is at least 0.5 µm, also preferred at least 1 µm and in another embodiment at least 1.5 µm. The method according to the present invention is particularly useful and advantageous when using particles having a critical particle size, as the inventive method deagglomerates the formed agglomerates even if the attraction forces between the particles increase.

The solvent that can be used for providing the suspension of step (a) can be any solvent or mixture of solvents that does not dissolve a significant amount of API. Preferably, the suspension that is prepared contains an amount of API in dissolved form of less than 10 wt.-%, further preferred of less than 5 wt.-%, even further preferred of less than 2 wt.-%. A suitable solvent and suitable amount of solvent can easily be determined by a person skilled in the art by suspending a certain amount of API in a solvent, separating the solution and the particles and weighing the solid particles to determine the amount of dissolved API. Preferably, the solvent is selected from the group consisting of water, ethanol, methanol, acetone, and dichlorometane. In a preferred embodiment, the solvent water is used.

Further preferred, the suspension of step (a) further comprises one or more excipients selected from the group consisting of hydrophilic excipients and polymers. Preferably, the hydrophilic excipient is selected from the group consisting of polyethylene glycols, poloxamers, polysaccharides, polyols, inorganic salts (e.g. sodium chloride), saccharides or mixtures thereof (e.g. StarLac® or IsoMalt®), lactose, spray dried lactose and starch, more preferably the hydrophilic excipient is selected from the group consisting of lactose, spray dried lactose and starch, even more preferably the hydrophilic excipient is lactose, and wherein the polymer is selected from the group consisting of polyvinyl alcohol, polyvinylpyrrolidone, gelatin or cellulose derivative such as methylcellulose, ethylcellulose, hydroxypropylmethylcellulose and hydroxypropylcellulose, preferably the cellulose derivative is hydroxypropylmethylcellulose. The use of excipients selected from the group of hydrophilic excipients and cellulose derivatives is particularly useful, for instance with regard to a (further) improved dissolution profile, e.g. based on the enhanced stabilization of the API particles by preventing a reagglomeration of the deagglomerated API particles.

In one embodiment of the invention, the suspension of step (a) only contains, as excipients, the excipients lactose and hydroxypropylmethylcellulose.

In general, the excipients that are used in the process described herein can either be added in dry form or in dissolved state, e.g. by dissolving the excipients in water and then adding the excipients to the pharmaceutical composition in steps (a), (b), (c) and/or (d).

In a further step (b), the suspension provided by step (a) is subjected to a high energy input treatment, so that essentially no agglomerates are present in the suspension. The high energy input treatment and suitable apparatuses that can be used in the process according to the present invention are described elsewhere herein. The high energy input treatment can be directly carried out to the suspension provided in step (a), but it is also possible to add e.g. further excipients as described elsewhere herein prior to applying the high energy input treatment.

Preferably, the suspension provided in step (a) is not subjected to a volume reducing step prior to carrying out the high energy input treatment. Reason for this is that the particle size of the API is not increased due to crystallization or precipitation processes upon solvent removal.

The high energy input treatment is carried out for a time that is suitable to deagglomerate essentially all agglomerates.

Within the meaning of the present invention, the high energy input treatment is such that essentially no agglomerates are present in the suspension after said high energy input step has been carried out. As already described elsewhere herein, agglomerates are secondary particles that consist of primary particles of API. The presence of agglomerates can be determined, if desired, by any suitable method that is known to a person skilled in the art. For instance, as described elsewhere herein, the requirement of "essentially no agglomerates are present in the suspension" is fulfilled if the particle size distribution d(0.5) of the particles when measured after the high energy treatment for deagglomeration corresponds essentially to or is smaller than the particle size distribution d(0.5) of the primary particles that are used for providing the suspension of step (a). With regard to the methods suitable for assessing whether this specific particle size distribution is fulfilled, reference is made to the description above.

Moreover, agglomeration can be assessed by Malvern: After measurement of a sample suspension, the ultrasound inside the Malvern mixing chamber can be used. If there is a reduction of the particle size distribution d(0.5) after having applied ultrasound to the sample suspension, there are still agglomerates present. The reduction of the particle size distribution d(0.5) can be correlated with the amount of agglomerates still present. A further possibility to determine whether the requirement "essentially no agglomerates are present" in the suspension is fulfilled is determining the amount of agglomerates being present in the suspension. Therein, the term "essentially no agglomerates" denotes that after having carried out the high energy input treatment not more than 20% by weight of the particles being present in the suspension are present as agglomerates, preferably not more than 10% by weight, even more preferably not more than 5% by weight and even more preferably not more than 3% by weight. Whether agglomerates are present, and if so, in which amount, can be measured e.g. as described above via Malvern.

If the majority of observed API particles is deagglomerated, i.e. not being present in an agglomerated state, as e.g. verifiable by one of the methods described above, the high energy method that was applied is suitable within the invention.

In order to assess the extent of agglomeration in a final dosage form, dissolution tests may be carried out. By doing so, preferably it may be further determined whether a final dosage form has been manufactured according to the inventive process, i.e. by providing a suspension comprising API particles and subjecting said suspension to a high energy input treatment, or whether the dosage form has been manufactured according to conventional methods. Such a dissolution test can for instance be carried out in a sodium lauryl sulphate (SDS) buffer having a pH of 7.0, using Apparatus 2, 50 rpm. If after 5 minutes more than about 15%, preferably more than about 16% of the API are dissolved, it can be concluded that deagglomerated API was present in the tested dosage form/pharmaceutical composition. Alternatively, or in addition to the dissolution test, the presence and, if desired, the extent, of agglomerates in the final dosage form can be determined by using SEM and optical images, as described elsewhere herein.

In a further embodiment according to the present invention, the high energy input step that is carried out in step (b) not only leads to a deagglomeration of essentially all agglomerates that are present in the suspension, but leads to a further reduction of the primary particle size, as e.g. measured by d(0.5). This reduction of the primary particle size may for instance be due to the application of two or more types of high energy input treatments, or due to the application of one type of high energy input treatment, however during an extended time period. "Extended time period" herein refers to a time period that is longer than that needed to ensure that essentially all agglomerates are deagglomerated. However, even if such a reduction of the primary particle size is carried out, by applying the method according to the present invention essentially no reagglomeration of the reduced API particles takes place. Without wishing to be bound by any theory, it is assumed that this prevention of reagglomeration is further contributed particularly to the excipients used (see above). Thus, in this further embodiment, during step (b) the particle size distribution d(0.5) is reduced, which means that it is less than 70% of the particle distribution d(0.5) of the primary particles that were used for providing the suspension of step a). In this embodiment, the particle size distribution d(0.5) can be assessed as indicated in (A) to (C) elsewhere herein.

In step c), the suspension prepared in step (b) is further processed. This further processing step comprises particular methods to further process the material after step (b). Preferably, the suspension obtained after step (b) is subjected to a high shear granulation, fluid bed granulation, spray drying or lyophilization step. Preferably, the suspension obtained after step (b) is sprayed onto a carrier, thereby obtaining the pharmaceutical composition. Spraying the suspension containing the API particles in deagglomerated form onto a carrier material allows (further) improving the pharmaceutical composition or dosage form, respectively, for instance in terms of (further) stabilizing the deagglomerated form of the API particles during further processing, e.g. by preventing the reagglomeration of the particles. When spray drying or fluid bed granulation is used in a preferred embodiment, the suspension provided in step b) is preferably not dried, e.g. not subjected to a volume reduction step by solvent removal, prior to fluid bed granulation or prior to spraying the suspension onto a carrier.

Suitable carriers are selected from the group consisting of lactose, such as lactose monohydrate and anhydrous lactose; starch and starch derivatives; mannitol; xylitol; sorbitol; cellulose such as microcrystalline cellulose and powdered cellulose; magnesium stearate; silica colloidal anhydrous; croscarmellose sodium; and mixtures thereof; preferably, the suitable carrier is selected from carriers being composed of water soluble material, preferably having a particle size equal to or below 100 µm or even equal to or below 50 µm (measured by sieve analysis), such as microcrystalline cellulose, croscarmellose sodium, lactose and/or their mixtures. A preferred carrier is a lactose carrier, having the above-defined particle size. As described below, the carrier material can also be subjected to a spraying process prior to spraying the suspension comprising the API that is practically insoluble in water as described onto the carrier. In this case, the practically insoluble API is provided onto the carrier that already comprises an API and/or excipients.

The ratio of the poorly soluble API(s)/carrier material can be any suitable ratio, preferably from 1/0.5 to 1/1000, more preferably the ratio of poorly soluble API(s)/carrier material is at least 1/1, and most preferably 1/5.

The process of spraying the suspension onto a carrier can be carried out by any methods commonly used in the art, preferably a fluidized bed process is applied.

Before or after spraying the suspension according to the present invention onto the carrier, it is also possible to spray other suspensions/solutions of excipients and/or API(s) onto the carrier.

The processes of high shear granulation and lyophilization are per se known to a person skilled in the art and can be carried out according to any suitable protocol. For instance, when carrying out high shear granulation, the deagglomerated suspension can be sprayed onto a carrier in a high shear granulator while mixing. The wet mass is further granulated for 5 to 20 minutes. Afterwards, it can be dried with vacuum inside the high shear mixer or it can be transferred to a fluid bed device for drying, or it can be dried in a tray. When carrying out lyophilization, the suspension can for instance be frozen, and the water is removed in order to obtain a dry powder which can later be mixed with excipients, e.g. with the excipients described elsewhere herein.

The pharmaceutical composition prepared in step (c) can then be formulated into a dosage form in a further step (d). Step (d) can e.g. comprise a drying step, a step of mixing the pharmaceutical composition comprising the carrier with the API with further excipients and then formulating the mixture preferably into a solid dosage form, including tablets, capsules (soft or hard capsules), caplets, lozenges, and sachets, preferably the dosage form is a tablet.

The method according to the present invention is particularly advantageous and useful if after step (b), e.g. during steps (c) or (d), in particular during step (d), compression forces are applied onto the pharmaceutical composition. By applying the method according to the present invention, the reagglomeration of the primary API particles present in the pharmaceutical composition is essentially avoided. Applying a high energy input treatment in combination with spray drying even further contributes to this effect. Without wishing to be bound by any theory it is assumed that by spraying the suspension containing API particles that are essentially deagglomerated onto carrier results in preserving the deagglomerated state of said API particles by fixing them on the carrier.

In one embodiment of the process according to the invention as described herein, step (a) comprises the step of (a1) providing a solution containing one or more excipients as defined herein, (a2) suspending the API(s) as defined herein in the solution of step (a1), and (a3) homogenizing the resulting suspension.

Within the context of the present invention, in one embodiment step (b) is directly carried out after step (a). This is in particular the case where no further API is added during step (a). It is also preferred that step (c) is directly carried out after step (b). This is in particular the case where no further excipient is added during step (b).

According to a further embodiment of the invention, at least one further excipient can be added during any of steps (a) to (d), preferably after step (a), more preferably after step (b).

The at least one further excipient can be selected from the group consisting of diluents, binding agents, fillers, disintegrants, lubricants, sweeteners, glidants, flavourings and colouring agents.

The fillers are preferably selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous or spray dried lactose, calcium, such as calcium hydrogenphosphate, sorbitol, and xylitol, particularly preferred, the fillers are selected from the group consisting of pregelatinized starch, microcrystalline cellulose, silicified microcrystalline cellulose, and lactose; most preferred, the filler is lactose;

the disintegrants are selected from the group consisting of carmellose calcium, carboxymethylstarch sodium, croscarmellose sodium, croscarmellose sodium salt (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrants are selected from the group consisting of sodium starch glycolate, croscarmellose sodium salt, crospovidone and croscarmellose sodium, and most preferred, the disintegrant is crospovidone; the lubricants are selected from the group consisting of stearic acid, talc, sodium stearyl fumarate and magnesium stearate, particularly preferred, the lubricant is magnesium stearate;

the binding agents are selected from the group consisting of polyvinyl pyrrolidone (Povidone), copolymers of vinylpyrrolidone with other vinyl derivatives (Copovidone), hydroxypropyl methylcellulose, methylcellulose, hydroxypropylcellulose, powdered acacia, gelatin, guar gum, carbomer, such as carbopol, polymethacrylates and starch, particularly preferred, the binding agents are selected from the group consisting of hydroxypropyl methylcellulose, hydroxypropylcellulose and copovidone, and most preferred, the binding agent is hydroxypropyl methylcellulose (hypromellose);

the diluents are selected from carbohydrates such as monosaccharides like glucose, oligosaccharides like sucrose, anhydrous lactose and lactose monohydrate, and sugar alcohols like sorbitol, mannitol, erythrol, and xylitol, particularly preferred the diluent is sorbitol;

glidants are selected from the group consisting of colloidal silica, hydrophobic colloidal silica and magnesium trisilicate, such as talcum, particularly preferred the glidants are selected from the group consisting of colloidal silica and hydrophobic colloidal silica; and/or sweeteners are selected from the group consisting of aspartame, saccharin sodium, dipotassium glycyrrhizinate, aspartame, stevia, thaumatin, and the like.

In the process as described herein, the dosage form can also be provided with a coating. Suitable coatings are known in the art and can e.g. be extended release coatings, intermediate coatings, and enteric coatings. Accordingly, the coating comprises one or more suitable components that are known to a person skilled in the art. In a preferred embodiment, the coating comprises one or more compounds selected from the group consisting of polymers, including cellulose derivatives (e.g. hypromellose), povidone, polyvinyl alcohol, polyethylene glycol, polymethacrylates, and insoluble compounds including titanium dioxide, pigments, lakes and talc. Preferably, the coating comprises hypromellose, polyethylene glycol, talc and suitable pigments.

The present invention also refers to a pharmaceutical composition obtained according to any of the preceding claims. Said pharmaceutical composition essentially comprises no agglomerates, i.e. secondary particles.

The present invention also refers to a pharmaceutical composition comprising particles of API on a carrier, wherein the API is practically insoluble in water, and wherein essentially no agglomerates of particles of said API are present in said composition and wherein preferably the particle size distribution d(0.5) of the API is less than 5 μm, preferably equal to or less than 4 μm, and most preferably equal to or less than 3 μm. The deagglomerated/agglomerated state can be analyzed by using SEM (scanning electron microscopy), Raman spectroscopy or by performing dissolution tests as described elsewhere herein. A deagglomerated state is present if not more than 50%, 40%, 30% or 20% of the observed particles are present as agglomerates, preferably not more than 10%, even more preferably not more than 5% and even more preferably not more than 3%.

The preferred API(s), carriers and excipients to be used in the pharmaceutical composition are described above.

Furthermore, the present invention relates to a pharmaceutical composition obtained by a process according to any of items (1) to (21).

The invention also relates to a dosage form, comprising the pharmaceutical composition according to the invention.

Preferably, the amount of the carrier with API(s) in the dosage form is in the range of 1 to 95 wt.-%, preferably in the range of 5 to 90 wt.-%, more preferably in the range of 10 to 70 wt.-% and even more preferably in the range of 30 to 60 wt.-% (respectively in % by weight relative to the whole adsorbate).

Furthermore, the present invention refers to the use of the dosage form according to the invention for the treatment of hypercholesterolemia.

DESCRIPTION OF THE FIGURES

FIG. 1 shows the dissolution profiles of the tablets prepared in Examples 1-4.

EXAMPLES

Comparative Example 1: Preparation of Tablets by Standard High Shear Wet Granulation Tablet Composition:

| Substance | Amount per tablet (mg) |
| --- | --- |
| Ezetimibe | 10.00 |
| Simvastatin | 80.00 |
| Microcrystalline cellulose | 120.00 |
| Lactose | 535.80 |
| Croscarmellose sodium | 24.00 |
| Hypromellose | 16.00 |
| Magnesium stearate | 12.00 |

-continued

| Substance | Amount per tablet (mg) |
|---|---|
| Citric acid | 2.00 |
| Butylated hydroxyanisole | 0.16 |
| Propyl galate | 0.04 |
| Total mass of the tablet | 800.00 |

Manufacturing Procedure:

Ezetimibe was blended with spray dried lactose and mixed in a high shear mixer. Simvastatin, microcrystalline cellulose, croscarmellose sodium and hydroxypropyl cellulose were added in the high shear mixer and the mixture was mixed again. Citric acid was dissolved in water, butylated hydroxyanisole and propyl galate were dissolved in ethanol. Water and ethanol solutions were mixed and used to granulate the powders in the high shear mixer. The resulting granulate was dried in a fluid bed apparatus, mixed with magnesium stearate and compressed into tablets.

Comparative Example 2: Preparation of Tablets by Fluid Bed Granulation without High Energy Input Tablet Composition:

| Substance | Amount per tablet (mg) |
|---|---|
| Ezetimibe | 10.00 |
| Simvastatin | 80.00 |
| Microcrystalline cellulose | 200.00 |
| Lactose | 476.00 |
| Croscarmellose sodium | 16.00 |
| Hypromellose | 10.00 |
| Magnesium stearate | 8.00 |
| Total mass of the tablet | 800.00 |

Manufacturing Procedure:

Ezetimibe and simvastatin were suspended in a solution of hypromellose in water and a part of lactose and mixed with a propeller mixer to prepare a homogenous suspension. Resulting suspension was sprayed onto microcrystalline cellulose, remaining lactose and croscarmellose sodium in a fluid bed apparatus. The resulting granulate was mixed with magnesium stearate and compressed into tablets.

Example 3: Preparation of Tablets By Using a Deagglomerated Suspension and Fluid Bed Granulation Tablet Composition:

| Substance | Amount per tablet (mg) |
|---|---|
| Ezetimibe | 10.00 |
| Simvastatin | 80.00 |
| Microcrystalline cellulose | 114.00 |
| Lactose | 557.60 |
| Croscarmellose sodium | 16.00 |
| Hypromellose | 10.00 |
| Magnesium stearate | 12.00 |
| Total mass of the tablet | 800.00 |

Manufacturing Procedure:

Simvastatin was suspended in a solution of hypromellose in water. The resulting suspension was sprayed onto microcrystalline cellulose, croscarmellose sodium and a part of lactose in a fluid bed apparatus. Ezetimibe was suspended in a solution of hypromellose and remaining lactose and mixed with a propeller mixer to prepare a homogenous suspension. The resulting suspension was passed through a ball mill, whereby the particle size distribution d(0.5) of ezetimibe remained essentially unchanged (Table 1). Resulting suspension was sprayed onto circulating powders in a fluid bed apparatus after simvastatin suspension. The resulting granulate was mixed with magnesium stearate and compressed into tablets.

TABLE 1

| Particle size of ezetimibe | | | |
|---|---|---|---|
| | D(0.1) [μm] | D(0.5) [μm] | D(0.9) [μm] |
| Starting particle size | 0.30 | 2.97 | 6.87 |
| Particle size after deagglomeration | 0.84 | 2.98 | 6.28 |

Example 4: Preparation of Tablets by Deagglomerated Suspension and Fluid Bed Granulation Tablet Composition:

| Substance | Amount per tablet (mg) |
|---|---|
| Ezetimibe | 10.00 |
| Simvastatin | 80.00 |
| Microcrystalline cellulose | 114.00 |
| Lactose | 557.60 |
| Butylated hydroxyanisole | 0.40 |
| Croscarmellose sodium | 16.00 |
| Hypromellose | 10.00 |
| Magnesium stearate | 12.00 |
| Total mass of the tablet (mg) | 800.00 |

Manufacturing Procedure:

Simvastatin was suspended in a solution of hypromellose in water. The resulting suspension was sprayed onto microcrystalline cellulose, croscarmellose sodium and a part of lactose in a fluid bed apparatus. Butylated hydroxyanisole was dissolved in ethanol and sprayed onto circulation powders in a fluid bed apparatus after simvastatin suspension. Ezetimibe was suspended in a solution of hypromellose and remaining lactose and mixed with a propeller mixer to prepare a homogenous suspension. The resulting suspension was further mixed with a high energy rotor-stator mixer (e.g. Ultra Turrax), whereby the particle size distribution d(0.5) of ezetimibe remained unchanged (Table 2). The resulting suspension was sprayed onto circulating powders in a fluid bed apparatus after butylated hydroxyanisole solution. The resulting granulate was mixed with magnesium stearate and compressed into tablets.

TABLE 2

| Particle size of ezetimibe | | | |
|---|---|---|---|
| | D(0.1) [μm] | D(0.5) [μm] | D(0.9) [μm] |
| Starting particle size | 0.30 | 2.97 | 6.87 |
| Particle size after deagglomeration | 0.83 | 2.54 | 5.03 |

Comparative Example 5: Preparation of Tablets by Dry High Shear Mixing and Compression Tablet Composition:

| Substance | Amount per tablet (mg) |
| --- | --- |
| Ezetimibe | 10.00 |
| Simvastatin | 80.00 |
| Microcrystalline cellulose | 160.00 |
| Lactose | 508.00 |
| Croscarmellose sodium | 12.00 |
| Hydroxypropyl cellulose | 16.00 |
| Colloidal silica | 6.00 |
| Magnesium stearate | 8.00 |
| Total mass of the tablet | 800.00 |

Manufacturing Procedure:

Ezetimibe (50% of micronized ezetimibe particles were below 3.9 micrometers) was blended with spray dried lactose and sieved through a sieve. Sieved mixture was mixed in a high shear mixer. Simvastatin, microcrystalline cellulose, croscarmellose sodium, hydroxypropyl cellulose and colloidal silica were added in the high shear mixer and the mixture was mixed again. The resulting mixture was sieved through a sieve, blended with magnesium stearate and compressed into tablets.

All tablet samples were analyzed on an USP Apparatus 2 (paddles) in a phosphate buffer with pH 7.0 containing sodium lauryl sulfate.

The dissolution profiles are of the tablets prepared in Comparative Examples 1, 2 and 5 and Examples 3 and 4 are shown in FIG. 1.

Example 6: Preparation of Tablets by Deagglomerated and Milled Suspension in Fluid Bed Apparatus Tablet Composition:

| Substance | Amount per tablet (mg) |
| --- | --- |
| Ezetimibe | 10.00 |
| Simvastatin | 80.00 |
| Microcrystalline cellulose | 108.00 |
| Lactose | 549.52 |
| Croscarmellose sodium | 24.00 |
| Hypromellose | 16.00 |
| Magnesium stearate | 12.00 |
| Butylated hydroxyanisole | 0.48 |
| Total mass of the tablet | 800.00 |

Manufacturing Procedure:

Butylated hydroxyanisole was dissolved in ethanol and sprayed onto microcrystalline cellulose, croscarmellose sodium and a part of lactose in a fluid bed apparatus. Simvastatin was suspended in a solution of hypromellose and lactose. The resulting suspension was sprayed onto circulation powders in a fluid bed apparatus after butylated hydroxyanisole solution. Ezetimibe was suspended in water in a solution of hypromellose and lactose and mixed with a high energy rotor-stator mixer (e.g. Ultra Turrax). Resulting suspension was further milled with ball mill and sprayed onto a part of lactose. The resulting simvastatin and ezetimibe granulates were mixed with microcrystalline cellulose and magnesium stearate and compressed into tablets.

TABLE 3

| | Particle size of ezetimibe | | |
| --- | --- | --- | --- |
| | D(0.1) [μm] | D(0.5) [μm] | D(0.9) [μm] |
| Starting particle size | 0.82 | 3.29 | 6.49 |
| Particle size after milling | 0.24 | 1.11 | 4.35 |

Example 7: Preparation of Ezetimibe Tablets by Deagglomerated and Milled Suspension in Fluid Bed Apparatus Tablet Composition:

| Substance | Amount per tablet (mg) |
| --- | --- |
| Ezetimibe | 10.00 |
| Lactose | 67.50 |
| Microcrystalline cellulose | 12.50 |
| Sodium Lauryl Sulfate | 2.00 |
| Croscarmellose sodium | 4.00 |
| Hypromellose | 2.50 |
| Magnesium stearate | 1.50 |
| Total mass of the tablet | 105.00 |

Manufacturing Procedure:

Ezetimibe was suspended in a solution of hypromellose and lactose in water and mixed with a high energy rotor-stator mixer (e.g. Ultra Turrax). The resulting suspension was further milled with a ball mill and sprayed onto the remaining part of the lactose. Sodium lauryl sulfate was dissolved in water and sprayed onto circulation powders in a fluid bed apparatus after the ezetimibe suspension. The resulting granulate was mixed with microcrystalline cellulose and magnesium stearate and compressed into tablets.

TABLE 4

| | Particle size of ezetimibe | | |
| --- | --- | --- | --- |
| | D(0.1) [μm] | D(0.5) [μm] | D(0.9) [μm] |
| Starting particle size | 0.83 | 2.76 | 5.19 |
| Particle size after milling | 0.63 | 1.99 | 5.49 |

The invention claimed is:

1. A pharmaceutical composition comprising:
   particles of a pharmaceutically active ingredient (API), wherein the solubility of the API is about 0.1 mg/ml or less in water, wherein the API is selected from a group consisting of ezetimibe, fenofibrate, sirolimus, ketoprofen, celecoxib, candesartan, atorvastatin, and simvastatin; and
   one or more excipients, and
   wherein the composition comprises essentially no agglomerates of the API particles,
   wherein the particle size distribution d(0.5) of the API is less than 3 μm, and
   wherein the pharmaceutical composition obtained by a process comprising:
   a) providing a suspension comprising the API particles and the one or more excipients;
   b) subjecting the suspension provided by step a) to a high energy input treatment, so that essentially no agglomerates are present in the suspension; and c) processing the suspension by high shear granulation, fluid bed granulation, spray drying or lyophilization.

2. The composition according to claim 1, wherein the one or more excipients is selected from a group consisting of a hydrophilic excipient and a polymer.

3. The composition according to claim 2, wherein the hydrophilic excipient is selected from a group consisting of polyethylene glycol, poloxamer, polyol, inorganic salt, polysaccharide, saccharide and mixtures thereof.

4. The composition according to claim 2 wherein the hydrophilic excipient is selected from a group consisting of lactose, spray dried lactose and starch.

5. The composition according to claim 2, wherein the polymer is selected from a group consisting of polyvinyl alcohol, polyvinylpyrrolidone, gelatin, methylcellulose, ethylcellulose, and hydroxypropylmethylcellulose.

6. The composition according to claim 1, wherein the excipients consist of lactose and hydroxypropylmethylcellulose.

7. A composition, comprising:
  particles of a pharmaceutically active ingredient (API) selected from a group consisting of ezetimibe, fenofibrate, sirolimus, ketoprofen, celecoxib, candesartan, atorvastatin, and simvastatin; and
  one or more excipients selected from a group consisting of polyethylene glycol, poloxamer, polyol, inorganic salt, polysaccharide, saccharide and mixtures thereof, polyvinyl alcohol, polyvinylpyrrolidone, gelatin, methylcellulose, ethylcellulose, and hydroxypropylmethylcellulose,
  wherein a solubility of the API is about 0.1 mg/ml or less in water,
  wherein the composition comprises essentially no agglomerates of the API particles, and
  wherein the particle size distribution d(0.5) of the API is less than 3 μm.

8. The composition of claim 7, wherein the polysaccharide is selected from a group consisting of lactose, spray dried lactose and starch.

9. The pharmaceutical composition of claim 1, wherein step a) comprises:
  a1) providing a solution containing one or more excipients;
  a2) suspending the API in the solution; and
  a3) homogenizing the resulting suspension.

10. A process for preparing the composition according to claim 7, comprising the steps of:
  a) providing a suspension comprising the API particles and the one or more excipients,
  b) subjecting the suspension provided by step a) to a high energy input treatment, so that essentially no agglomerates are present in the suspension, and
  c) further processing the suspension by high shear granulation, fluid bed granulation, spray drying or lyophilisation.

11. The process according to claim 10, wherein after step (c) a further step (d) of formulating the composition into a dosage form is carried out.

12. The process according to claim 10, wherein the primary particle size distribution d(0.5) of the API that is used for providing the suspension of step (a) is less than about 5 μm.

13. A composition comprising:
  ezetimibe particles;
  microcrystalline cellulose;
  lactose;
  croscarmellose sodium;
  hypromellose; and
  magnesium stearate,
  wherein the composition comprises essentially no agglomerates of ezetimibe, and
  wherein the particle size distribution d(0.5) of the ezetimibe particles is less than 3 μm.

14. The composition of claim 13, wherein the ezetimibe particles are in an amount of less than about 10 weight percent of the composition.

15. The composition of claim 13, further comprising simvastatin.

16. The composition of claim 13, wherein:
  the ezetimibe particles are provided in an amount of 10 mg;
  the microcrystalline cellulose is provided in an amount of 12.5 to 114 mg;
  the lactose is provided in an amount of 67.5 to 557.6 mg;
  the croscarmellose sodium is provided in an amount of 4 to 24 mg;
  the hypromellose is provided in an amount of 2.5 to 16 mg; and
  the magnesium stearate is provided in an amount of 1.5 to 12 mg.

* * * * *